United States Patent
Hill

(10) Patent No.: US 9,936,878 B2
(45) Date of Patent: *Apr. 10, 2018

(54) COMMUNICATIONS NETWORK FOR DISTRIBUTED SENSING AND THERAPY IN BIOMEDICAL APPLICATIONS

(75) Inventor: Gerard J. Hill, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 862 days.

This patent is subject to a terminal disclaimer.

(21) Appl. No.: 13/086,519

(22) Filed: Apr. 14, 2011

(65) Prior Publication Data

US 2011/0196451 A1    Aug. 11, 2011

Related U.S. Application Data

(63) Continuation of application No. 11/739,388, filed on Apr. 24, 2007, now Pat. No. 7,949,404.

(60) Provisional application No. 60/805,787, filed on Jun. 26, 2006.

(51) Int. Cl.
| | | |
|---|---|---|
| *A61N 1/36* | (2006.01) | |
| *A61B 5/00* | (2006.01) | |
| *A61N 1/372* | (2006.01) | |
| *G06F 19/00* | (2018.01) | |

(52) U.S. Cl.
CPC ........ *A61B 5/0031* (2013.01); *A61N 1/37282* (2013.01); *A61N 1/37288* (2013.01); *G06F 19/3418* (2013.01)

(58) Field of Classification Search
USPC .......................... 600/300; 607/30–32, 59–61
See application file for complete search history.

(56) References Cited

U.S. PATENT DOCUMENTS

| | | |
|---|---|---|
| 4,886,064 A | 12/1989 | Strandberg |
| 4,987,897 A | 1/1991 | Funke |
| 5,113,859 A | 5/1992 | Funke |
| 5,558,640 A | 9/1996 | Pfeiler et al. |
| 5,620,475 A | 4/1997 | Magnusson |
| 5,721,733 A | 2/1998 | Wang et al. |
| 5,861,018 A | 1/1999 | Feierbach |
| 6,185,452 B1 | 2/2001 | Schulman et al. |
| 6,239,724 B1 | 5/2001 | Doron et al. |
| 6,249,703 B1 | 6/2001 | Stanton et al. |

(Continued)

FOREIGN PATENT DOCUMENTS

| | | |
|---|---|---|
| EP | 1022035 A1 | 7/2000 |
| EP | 1524619 A2 | 4/2005 |

(Continued)

OTHER PUBLICATIONS (PCT/US2008/059103) PCT Notification of Transmittal of the International Search Report and the Opinion of the International Searching Authority, dated Oct. 23, 2008, 6 pages.

(Continued)

*Primary Examiner* — Carl H Layno
*Assistant Examiner* — Jennifer Ghand

(57) ABSTRACT

An implantable medical device system is provided with multiple medical devices implanted in a patient's body and a wireless mesh communication network providing multiple communication pathways between the multiple medical devices. A communication pathway between a first and a second implanted device of the multiple medical devices can comprise one or more of the other implanted multiple medical devices.

13 Claims, 5 Drawing Sheets

(56) References Cited

U.S. PATENT DOCUMENTS

| | | |
|---|---|---|
| 6,411,842 B1 | 6/2002 | Cigaina et al. |
| 6,418,346 B1 | 7/2002 | Nelson et al. |
| 6,442,433 B1 | 8/2002 | Linberg |
| 6,480,745 B2 | 11/2002 | Nelson et al. |
| 6,482,154 B1 | 11/2002 | Haubrich et al. |
| 6,592,518 B2 | 7/2003 | Denker et al. |
| 6,599,250 B2 | 7/2003 | Webb et al. |
| 6,622,045 B2 | 9/2003 | Snell et al. |
| 2001/0031998 A1 | 10/2001 | Nelson et al. |
| 2002/0032470 A1 | 3/2002 | Linberg |
| 2002/0032720 A1 | 3/2002 | Nelson et al. |
| 2003/0114898 A1 | 6/2003 | Von Arx et al. |
| 2003/0220673 A1 | 11/2003 | Snell |
| 2003/0223514 A1 | 12/2003 | Pladdy et al. |
| 2003/0229383 A1 | 12/2003 | Whitehurst et al. |
| 2004/0015058 A1 | 1/2004 | Besson et al. |
| 2005/0113885 A1 | 5/2005 | Haubrich et al. |
| 2005/0117526 A1 | 6/2005 | Melnik |
| 2005/0197680 A1 | 9/2005 | DelMain et al. |
| 2005/0201454 A1 | 9/2005 | Chaudhuri et al. |
| 2005/0276255 A1 | 12/2005 | Aiello et al. |
| 2006/0007863 A1 | 1/2006 | Naghian |
| 2006/0009818 A1 | 1/2006 | Von Arx et al. |
| 2006/0031378 A1 | 2/2006 | Vallapureddy et al. |
| 2006/0067440 A1 | 3/2006 | Hsu et al. |
| 2006/0083186 A1 | 4/2006 | Handforth et al. |
| 2006/0092855 A1 | 5/2006 | Chiu |
| 2006/0122667 A1 | 6/2006 | Chavan et al. |
| 2006/0149329 A1 | 7/2006 | Penner |
| 2006/0224213 A1 | 10/2006 | Fuller et al. |
| 2006/0258322 A1 | 11/2006 | Conner et al. |
| 2007/0239229 A1 | 10/2007 | Masoud et al. |
| 2007/0251835 A1 | 11/2007 | Mehta et al. |
| 2007/0273504 A1 | 11/2007 | Tran |
| 2007/0299480 A1 | 12/2007 | Hill |
| 2008/0046038 A1 | 2/2008 | Hill et al. |
| 2008/0300660 A1 | 12/2008 | John |

FOREIGN PATENT DOCUMENTS

| | | | |
|---|---|---|---|
| WO | 9700708 | A1 | 1/1997 |
| WO | 0143823 | A1 | 6/2001 |
| WO | 03033070 | A1 | 4/2003 |
| WO | 03095024 | A2 | 11/2003 |
| WO | 05112216 | A2 | 11/2005 |

OTHER PUBLICATIONS

EP Application No. 07798144.7, Communication Pursuant to Article 94(3), EPC, dated Mar. 12, 2012, 4 pages.

PCT/US2008/059103, International Preliminary Report on Patentability and the Written Opinion of the International Searching Authority, dated Oct. 27, 2009, 6 pages.

PCT/US2007/070463, International Preliminary Report on Patentability and the Written LOpnion of the International Searching Authority, dated Jan. 6, 2009, 11 pages.

EP Application No. 07798144.7, Communication Pursuant to Article 94(3), EPC, dated Aug. 31, 2012, 6 pages.

Lee et al, "A Workload-Based Adaptive Load-Balancing Technique for Mobile Ad Hoc Networks", Wireless Communications and Networking Conference, 2005 IEEE, vol. 4, Mar. 13, 2005, pp. 2002-2007.

Singh et al., "Power-Aware Routing in Mobile Ad Hoc Networks", Mobiocom '98, Proceedings of the 4th Annual ACM/IEEE International Conference on Mobile Computing and Networking, Oct. 25, 1998, pp. 181-190.

COMMUNICATIONS NETWORK FOR DISTRIBUTED SENSING AND THERAPY IN BIOMEDICAL APPLICATIONS

CROSS REFERENCE TO PRIORITY APPLICATION

This application is a continuation application of U.S. application Ser. No. 11/739,388 filed Apr. 24, 2007, now allowed U.S. Pat. No. 7,949,404, which claims priority to application Ser. No. 60/805,787, filed Jun 26, 2006 and entitled, "Communications Network for Distributed Sensing and Therapy in Biomedical Applications", which is incorporated by reference herein.

TECHNICAL FIELD

The invention relates generally to implantable medical device systems and, in particular, to a communications network for use with implantable sensing and/or therapy delivery devices organized in a distributed, mesh network.

BACKGROUND

A wide variety of implantable medical devices (IMDs) are available for monitoring physiological conditions and/or delivering therapies. Such devices may includes sensors for monitoring physiological signals for diagnostic purposes, monitoring disease progression, or controlling and optimizing therapy delivery. Examples of implantable monitoring devices include hemodynamic monitors, ECG monitors, and glucose monitors. Examples of therapy delivery devices include devices enabled to deliver electrical stimulation pulses such as cardiac pacemakers, implantable cardioverter defibrillators, neurostimulators, and neuromuscular stimulators, and drug delivery devices, such as insulin pumps, morphine pumps, etc.

IMDs are often coupled to medical leads, extending from a housing enclosing the IMD circuitry. The leads carry sensors and/or electrodes and are used to dispose the sensors/electrodes at a targeted monitoring or therapy delivery site while providing electrical connection between the sensor/electrodes and the IMD circuitry. Leadless IMDs have also been described which incorporate electrodes/sensors on or in the housing of the device.

IMD function and overall patient care may be enhanced by including sensors distributed to body locations that are remote from the IMD. However, physical connection of sensors distributed in other body locations to the IMD in order to enable communication of sensed signals to be transferred to the IMD can be cumbersome, highly invasive, or simply not feasible depending on sensor implant location. An acoustic body bus has been disclosed by Funke (U.S. Pat. No. 5,113,859) to allow wireless bidirectional communication through a patient's body. As implantable device technology advances, and the ability to continuously and remotely provide total patient management care expands, there is an apparent need for providing efficient communication between implanted medical devices distributed through a patient's body or regions of a patient's body, as well as with devices.

DETAILED DESCRIPTION

Figure 1:
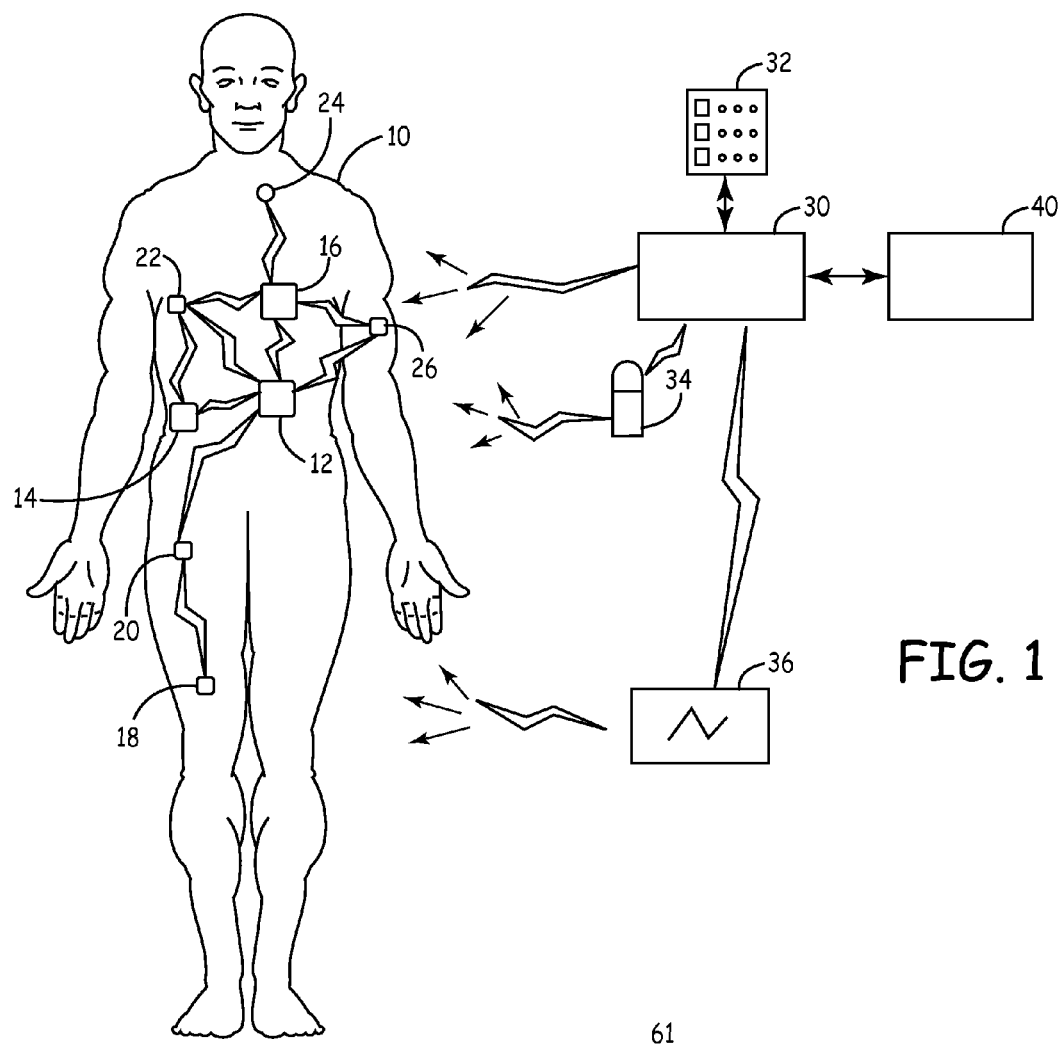
FIG. 1 is a schematic diagram of a wireless communication network implemented in an implantable medical device system.

The present invention is directed to providing a communications network implemented in an implantable medical device system, wherein the network is configured as a mesh network that allows data to be routed between implanted and external devices as needed via continuously available connections established through node-to-node routes that can include multiple node "hops." In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. As used herein, the term "node" refers to a device included in a wireless mesh network capable of at least transmitting data on the network and may additionally include other functions as will be described herein. Each "node" is a "network member" and these terms are used interchangeably herein. A node can be either an implanted or an external device. The wireless mesh network generally includes multiple implantable devices each functioning as individual network nodes in a mesh architecture and may include external devices functioning as equal network nodes as will be further described herein. It is recognized that an overall medical device system implementing a mesh communication network may further include non-networked devices (implantable or external).

FIG. 1 is a schematic diagram of a wireless communication network implemented in an implantable medical device system. The wireless communication network is characterized by a mesh architecture that allows multi-hop communication across network nodes. The network includes multiple implantable devices 12 through 26 each functioning as a node (network member).

The network may further include external devices functioning as equal nodes. Patient 10 is implanted with multiple medical devices 12 through 26 each of which may include physiological sensing capabilities and/or therapy delivery capabilities. As will be further described herein, some of the implanted devices 12 through 26 may be implemented as specialty nodes for performing specific network functions such as data processing, data storage, or communication management functions without providing any physiological sensing or therapy delivery functions.

For example, device 12 may be a therapy delivery device such as a cardiac pacemaker, implantable cardioverter defibrillator, implantable drug pump, or neurostimulator. Device 16 may also be a therapy delivery device serving as a two-way communication node and may further be enabled for performing specialty network management functions such as acting as a network gateway. Device 14 may be embodied as a sensing device for monitoring a physiological condition and also serve as a two-way communication node. Devices 18, 22, 24, and 26 may be embodied as sensing devices for monitoring various physiological conditions and may be implemented as low-power devices operating primarily as transmitting devices with no or limited receiving capabilities. Device 20 may be implemented as a repeater node for relieving the power requirement burden of sensing device 18 for transmitting data from a more remote implant location to other network nodes. The mesh network is an n-dimensional network wherein node depth may be defined spatially with respect to proximity to a specialized node, such as a node incorporating gateway, data processing or data storage capabilities.

Implantable devices that may be included as mesh network members include any therapy delivery devices, such as those listed above, and any physiological sensing devices such as EGM/ECG sensors, hemodynamic monitors, pressure sensors, blood or tissue chemistry sensors such as oxygen sensors, pH sensors, glucose sensors, potassium or other electrolyte sensors, or sensors for determining various protein or enzyme levels. The mesh network communication system provided by various embodiments of the present invention is not limited to any specific type or combination of implantable medical devices.

The mesh network communication system allows a multiplicity of devices to be implanted in a patient as dictated by anatomical, physiological and clinical need, without restraints associated with leads or other hardwire connections through the body for communicating signals and data from one device to another. As such, sensors and/or therapy delivery devices may be implanted in a distributed manner throughout the body according to individual patient need for diagnostic, monitoring, and disease management purposes. Data from the distributed system of implanted sensors and/or therapy delivery devices is reliably and efficiently transmitted between the implanted devices for patient monitoring and therapy delivery functions and may be transmitted to external devices as well for providing patient feedback, remote patient monitoring etc.

The implanted devices 12 through 26 may rely on various power sources including batteries, storage cells such as capacitors or rechargeable batteries, or power harvesting devices relying for example on piezoelectric, thermoelectric or magnetoelectric generation of power. The mesh network allows management of communication operations to be performed in a way that minimizes the power burden on individual devices (nodes) and can eliminate functional redundancies within the overall system. The distributed devices can be provided having minimal power requirements and thus reduced overall size. Implantable devices functioning as network nodes may be miniaturized devices such as small injectable devices, devices implanted using minimimally invasive techniques or mini-incisions, or larger devices implanted using a more open approach.

The mesh network may include external devices as shown in FIG. 1 such as a home monitor 30, a handheld device 34, and external monitoring device 36. Reference is made to commonly-assigned U.S. Pat. No. 6,249,703 (Stanton et. al.) regarding a handheld device for use with an implantable medical device, hereby incorporated herein by reference in its entirety. The medical device system may further include external devices or systems in wireless or wired communication with external mesh networked devices such as a patient information display 32 for displaying data retrieved from the mesh network to the patient, and a remote patient management system 40. Physiological and device-related data is available to any device (node) included in the mesh network, and aggregated data can be used to provide short-loop feedback to the patient or caregiver via the home monitor 30 and patient information display 32. The home monitor 30, in this illustrative example, includes RF receiver and long range network functionality allowing data received from the implanted network nodes to be accumulated and prioritized for further transmission to the remote patient management system 40 and/or patient information display 32. The patient can respond appropriately to information retrieved from the mesh network and displayed on patient information display 32 in accordance with clinician instructions. A patient may respond, for example, by modifying physical activity, seeking medical attention, altering a drug therapy, or utilizing the handheld device 34 to initiate implanted device functions.

Data can also be made available to clinicians, caregivers, emergency responders, clinical databases, etc. via external or parallel communication networks to enable appropriate and prompt responses to be made to changing patient conditions or disease states. Aggregated data can be filtered, prioritized or otherwise adjusted in accordance with patient condition and therapy status to provide clinically meaningful and useful information to a clinician or remote patient management system in a readily-interpretable manner. The home monitor 30 may function as a network administration node receiving patient and device-related data from the implanted nodes in a continuous, periodic, or triggered manner and managing transmissions of the aggregated data to other networks or devices. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions of network communication systems for use with implantable medical devices for remote patient monitoring and device programming, all of which are hereby incorporated herein by reference in their entirety.

Home monitor 30 and/or a programmer may be used for communicating with one or more of implanted devices 12 through 26 using bidirectional RF telemetry for programming and/or interrogating operations. Reference is made to commonly-assigned U.S. Pat. No. 6,482,154 (Haubrich et al.), hereby incorporated herein by reference in its entirety, for an example of one appropriate long-range telemetry system for use with implantable medical devices.

The mesh architecture allows network communication between nodes to make multiple hops. Communication paths between nodes illustrated in FIG. 1 are only examples of some of the shortest pathways existing between adjacent nodes. Communication paths will exist between each node and every other node in the network. Multiple hops may be made between nodes, in accordance with individual node roles, node power status, channel plan and routing scheme, each of which will be further described herein.

The mesh network is a self-configuring network in which all nodes are initially equal status, i.e. the nodes do not function in a master-slave relationship as provided in other kinds of networking schemes. As used herein, the terms "self-configuration" and "reconfiguration" refer to the network's ability to automatically adjust node roles and assignments, the network channel plan, and the network routing scheme, all of which will be further described below. "Primary" node functions, as used herein, generally refers to device functions relating to patient care such as physiological sensing or therapy delivery functions, whereas the term "network" functions refers generally to roles, assignments or tasks that the device performs as part of the mesh communication network. Some network nodes will be enabled to perform only network functions without any primary sensing or therapy delivery functions.

Initially, the network will enter a learning mode during which the network members learn about all other network members. Each node includes memory allocated for storing a preliminary network rule set. The rule set defines communication priorities and may provide a preliminary channel plan. During the learning mode, individual nodes are assigned tasks or network functions based on the node functional capacity and power capacity relative to other network members, the node primary function and the preliminary network rules. Each node learns the functions performed by other nodes and begins to take on specialist roles as the network learns about the overall group functionality and membership. Node roles will be described in greater detail below.

A communications routing scheme is formed based on patient status and the power status of each node. The routing scheme prioritizes data communications such that data relating to clinically significant events or conditions is given priority over data that does not have immediate or serious impact on the patient's well-being.

New nodes may be introduced at any time with the network performing a self-configuring re-learning process to grow "organically" and thereby incorporate the new node and adjust node roles and the routing scheme as appropriate. As such, a patient may initially be implanted with nodes functioning as sensing devices used to monitor physiological conditions for diagnostic purposes. After a diagnosis is made, a treatment plan may involve implanting one or more therapy delivery devices. When a new therapy delivery device is added, the network will perform a re-learning process to adjust node roles and the routing scheme to maintain node communication priorities and optimal communications reliability and efficiency in accordance with the governing or an adjusted network rule set. As new nodes are added, the new nodes would seamlessly integrate into the network. In order to do this, the network membership, the existing network rule set and the node's primary function and power source would be factored into a new operating rule set, new pecking order between nodes, new node roles, new routing scheme and new channel plan.

The mesh network is a self-healing network. Nodes may drop out of the network, for example, due to power loss, deactivation, or removal from the patient. Sensing devices implanted for diagnostic purposes may be removed as the patient enters a treatment plan with new therapy delivery devices being implanted. Sensing or therapy delivery devices may be replaced by newer models or models having expanded capabilities. When a node is removed from the network, either physically or functionally, a self-healing process will reconfigure the node roles, channel plan, and routing scheme.

An initial network rule set stored in the memory of each node at initiation of the network may be altered or reconfigured externally through a designated communications channel by a network administrator or authorized personnel using an external programming device. An external change to the network rules will re-trigger the learning process such that all node roles and the routing scheme are redefined according to the new rules, current patient conditions and the power status of individual nodes.

Figure 2:
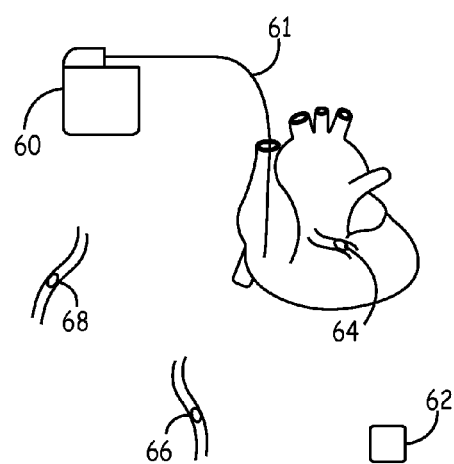
FIG. 2 is a schematic diagram of one example of a mesh communication network including multiple implantable medical devices.

FIG. 2 is a schematic diagram of one example of a mesh communication network including multiple implantable medical devices. An implantable cardiac stimulation device 60 is coupled to a patient's heart by a lead 61. In addition to components such as sensing circuitry, pulse generator circuitry, and timing and control modules typically included in a cardiac stimulation device, device 60 includes a battery as a power source for network communications, memory for storing network rules, and a wireless transceiver for bidirectional communication on the mesh network. Additional network nodes include distributed sensors 64, 66 and 68. Sensors 64, 66, and 68 may be physiological sensors for monitoring blood pressure, blood or tissue chemistry, blood flow, or other biological signals at various implant locations. Sensors 64, 66, and 68 each include a power source (which may be a storage device such as rechargeable battery or capacitor, an energy harvesting device, or a stand-alone battery), a physiological sensor, and a transmitter or transceiver for communicating on the mesh network. Sensors 64, 66, and 68 may be implanted at various targeted monitoring sites without the limitations normally associated with lead-based sensors. However, it is recognized that network node devices may include lead-based as well as leadless devices.

Device 62 is embodied as a specialized network node for performing network tasks such as data processing and storage. Device 62 is provided without primary physiological sensing or therapy delivery capabilities. As such device 62 generally includes a power source, a processor for executing communication operations, a memory for storing network rules and patient and device data, and a transceiver for communicating on the mesh network. Device 62 may receive data from sensors 64, 66, 68 as well as cardiac stimulation device 60 and perform data processing algorithms, transmit results back to the cardiac stimulation device for use in therapy control, transmit results to an external device (node), store data for future transmission to an external device, etc. Device 62 allows hardware and functional redundancies such as data processing capabilities and storage to be removed from the networked system, thereby allowing a reduction in the size and power requirements of other individual nodes. As such, sensors 64, 66, and 68 may be miniaturized and execute primary sensing functions with minimal or no data processing and storage. Sensed data is transferred to device 62 for processing, storing or transmission to other network nodes.

Figure 3:
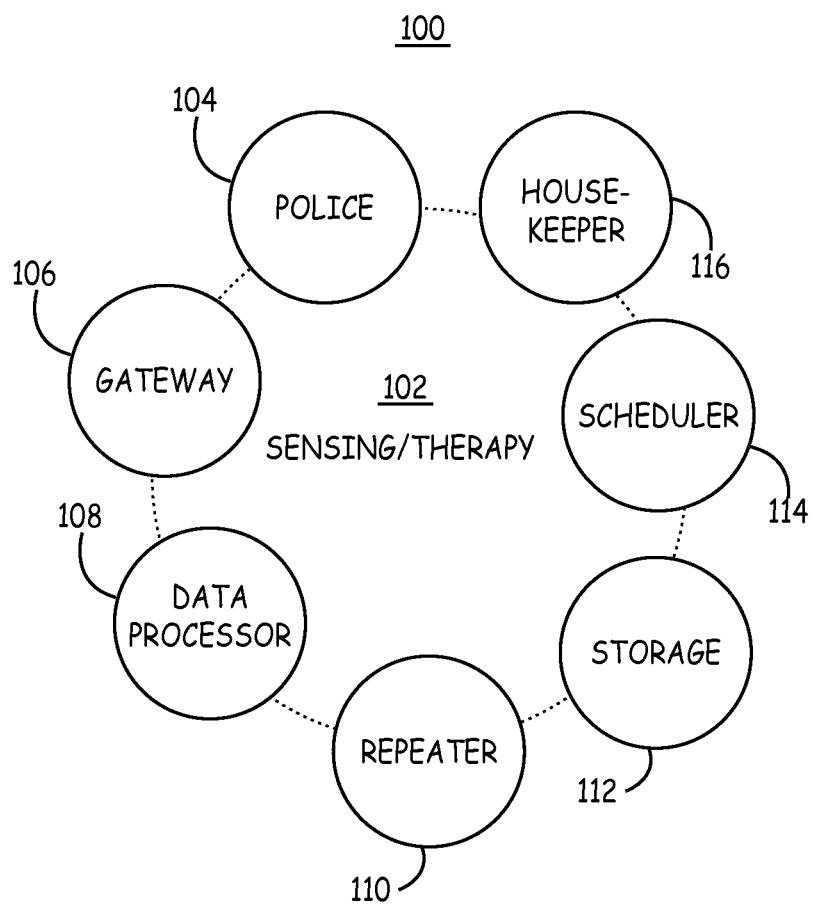
FIG. 3 is a conceptual diagram depicting the specialized roles that may be assigned to network nodes.

FIG. 3 is a conceptual diagram depicting the specialized roles that may be assigned to network nodes. Network node 100 represents any implanted device included as a member of the mesh network. Node 100 is configured to primarily perform physiological sensing and/or therapy delivery functions 102. In addition to the primary sensing and/or therapy delivery functions 102, node 100 may be assigned specialized network tasks. Examples of specialized network tasks are illustrated in FIG. 3 and include, but are not limited to, network police 104, gateway 106, data processing 108, repeater 110, storage 112, scheduler 114, and housekeeper 116. In some embodiments, implanted device 100 may be implemented solely for purposes of performing specialized network functions without being configured to perform primary sensing or therapy delivery functions 102. Other specialist node roles may include an "algorithm workhorse" node for performing complex, processing power intensive algorithms and a "local coordinator" for coordinating communication operations within localized clusters or neighborhoods of nodes.

A node assigned the role of police node 104 is provided for monitoring inappropriate behavior of any of the network members. Inappropriate behavior includes, for example, excessive communications in terms of frequency and/or data size, erroneous data generation, or other "deviant" behaviors. The police node 104 may be configured to have the authority to reconfigure a node which is determined to be functioning inappropriately on the network. The reconfiguration may include temporarily or permanently disabling the node as a network member, logically isolating the data communications from the deviant node by flagging messages with a logical identifier, allowing data to be removed from aggregated data upstream, or reassigning the node to a low priority in the routing scheme and channel plan. The primary, non-network functions of the deviant node may remain unchanged such that any sensing or therapy delivery operations may continue according to normal device operation. In some embodiments, the police node may have the authority to also alter the primary, non-network functions, for example if inappropriate device function is suspected, the police node may be authorized to temporarily or permanently suspend or alter primary device functions. Alternatively the police node may issue a notice of the suspected inappropriate function which is channeled through the network to allow patient and/or clinician notification.

An implanted node functioning as a gateway node 106 is assigned the task of coordinating communications with another network or device outside of the mesh network. The gateway node 106 may schedule, select and prioritize data being transmitted to an external network or device. The gateway node 106 may be authorized to take control over one or more channels for external or special data transmissions and communicate to other network members that those channels are temporarily unavailable. The gateway node 106 will execute translation, security or other protocols required for transferring data to another network. The gateway node may have a larger power source, longer communication range, and connectivity with other network technologies such as WiFi 802.11, ZigBee 802.15.4, Bluetooth, CDMA, GSM, etc. If a gateway node is not present or assigned by the network membership, then individual nodes may be enabled to communicate with external networks or devices as needed. The ability to communicate to external devices/networks may be a programmable parameter for each node, and can be adjusted dynamically as the network changes.

A data processor node 108 is a node configured with greater power capacity and/or processing power than other network members. Data processor node 108 may be assigned processing tasks for other network members or the network as a whole to relieve the power and processing burden of other individual network members. Data processor node 108 may be provided with the processing power to execute complex, power-intensive algorithms that are difficult to implement in smaller-sized nodes.

A repeater node 110 provides "shortcut" connectivity to remote nodes. As discussed previously in conjunction with FIG. 1, a node implanted in a "deeper layer" of the mesh network may transmit data to/from higher layers or specialized nodes via a repeater node, thereby relieving the power burden placed on a remote node or other intervening nodes for performing network communications.

A storage node 112 is a node configured with greater memory capacity than other network members and is assigned the task for storing data received from network members. Such data may be transmitted from storage node 112 to other network members as appropriate. For example data processor node 108, gateway node 106, or a therapy delivery node 102 may send data requests to storage node 112.

A scheduler node 114 may perform network scheduling tasks such as scheduling data transmissions between implanted and external nodes and scheduling network "meetings." Network "meetings" may be scheduled when reconfiguration of the node assignments and roles is needed in response to a change in patient condition, a change in power status of one or more individual nodes, a change in network membership (a new node introduced or an existing node removed from the network), or when new network rules are programmed from an external source. In general, scheduler node 114 is assigned the task of coordinating network activities that involve all or any subset of network members. This task of coordinating network activities generally includes "waking up," or scheduling a "waking up", of all or any subset of network members for performing a specified activity. Network nodes are generally in a low-power "alert" state that allows them to be "woken up" by another network node. Upon receiving a "wake-up" signal, the node converts to a high power "awake" state ready to receive data transmissions or commands.

A housekeeper node 116 is assigned the task of monitoring the channel plan to ensure that the plan is efficient and well-organized in terms of the number of nodes and communication workload assigned to each channel. The housekeeper node 116 ensures that all members have an up-to-date channel plan and may alter the plan in response to changes in communication priorities, patient condition and the power status of individual nodes.

The network roles illustrated in FIG. 3 are examples of the types of roles that individual nodes may be assigned and though these roles have been described in the context of a node embodied as an implantable device, external devices may also be assigned specialist node roles. Any one node may include one or more of the roles depicted and described. The roles included in a mesh communication network implemented in an implantable medical device system will vary depending on the particular application. The assignments of those roles can vary over the operating life of the medical device system as the network performs self-configuring and self-healing processes in response to changes in network membership, changes in network rules, changes in patient status, and changes in power status of individual nodes.

Figure 4:
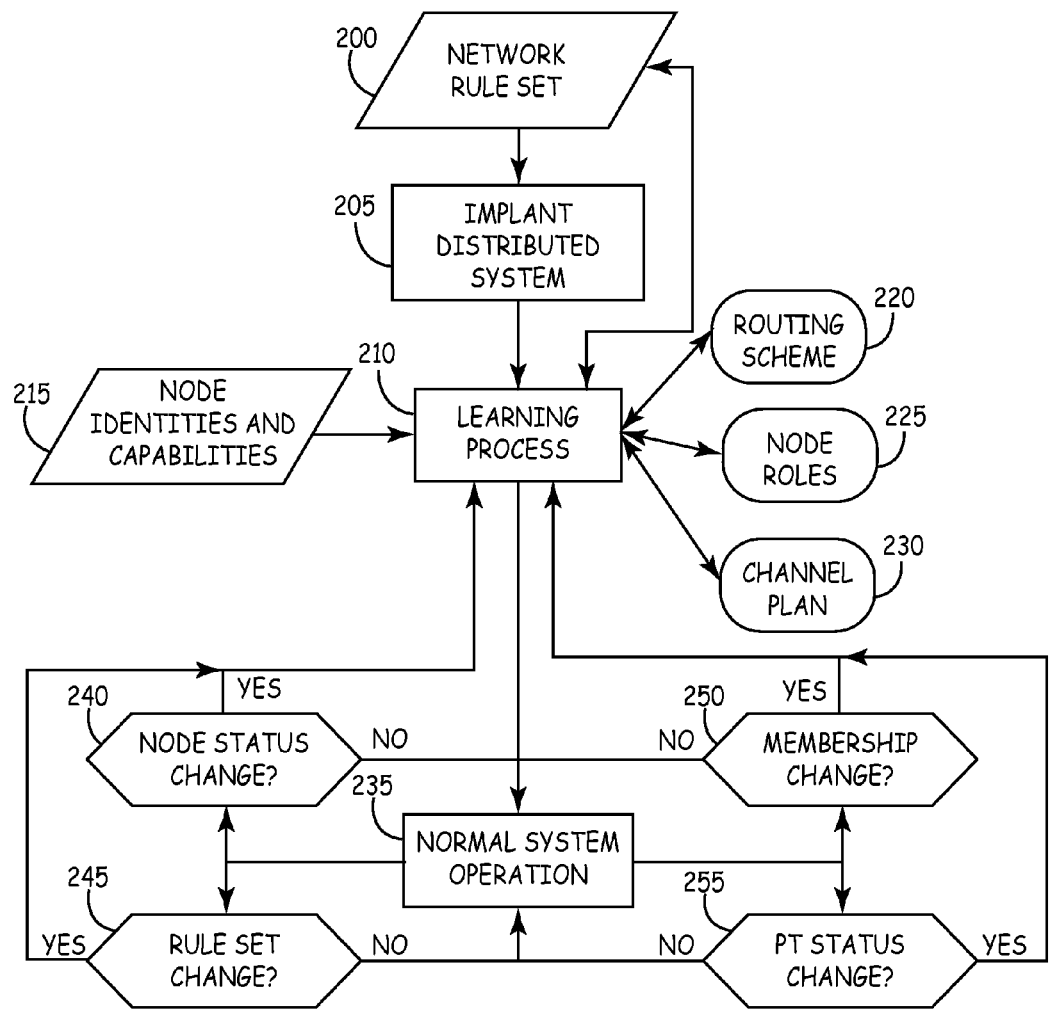
FIG. 4 is a flow diagram providing an overview of the general operation of a mesh network implemented in an implantable medical device system.

FIG. 4 is a flow diagram providing an overview of the general operation of a mesh network implemented in an implantable medical device system. At block 200, a network rule set is provided and stored in the memory of each system device to be included in the mesh network. The rule set defines an initial channel plan shared by all network members and priority communication rules. The rule set may be implemented in a look-up table and can be altered, adjusted or replaced at any time by a network administrator.

The rule set may include constant rules and variable rules. The variable rules are derived during self-configuring processes and are dynamically updated in response to changing node membership, changes in node operating and power status, and changes in patient status or as otherwise programmed by a user. The constant rules establish generally unalterable operating network conditions.

The constant rules may apply to the channel plan (e.g., certain channels may be emergency-use only or reserved for external communication); message length (to set baseline for message coexistence and communication success); maximum message redundancy; maximum/minimum update rate; maximum message repeat level; controls on maximum mesh depth thereby limiting power usage due to node hopping; pre-defined pecking order for device/sensor communication; and pre-defined pecking order for device/sensor power based attributes (e.g., a therapy delivery device having a primary battery may be assigned a power rating of 10, whereas a simple infrequent sensor may have a power rating in the 1-3 range in accordance with the power supply for the given node or device). On infrequent occasions, constant rules included in a rule set may be altered, for example in order to accommodate next generation nodes implementing a new operation system or operating system updates.

At block 205, selected devices are implanted in a patient in a distributed manner, including sensing devices and/or therapy delivery devices and optionally including specialist node devices (repeaters, data storage, data processors, etc.). When the devices are positioned within communication proximity to each other, and any external devices that are enabled to communicate on the mesh network, the mesh network will initiate a self-configuring process at block 210. All nodes are initially equal entering the learning process 210. During this process 210, the network "learns" the identities and capabilities (input block 215) of all of its members. Individual node roles 225, a routing scheme 220, and a channel plan 230 will be developed and established within the operational constraints and communication priorities provided by the network rule set and based on the functionality and power status of each node.

The system operates normally at block 235 carrying on sensing and/or therapy delivery functions according to programmed operating modes. Data communications on the mesh network will occur during normal system operation 235 in response to previously scheduled, triggered, or requested data transmissions in accordance with the established node assignments, routing scheme and channel plan.

Throughout normal system operation, any change in the network operating conditions or environment, such changes in individual node status (block 240), network rule set (block 245), node membership (block 250), or patient status (block 255), can cause a reconfiguration to occur. Other conditions that may cause the network to reconfigure may include a clinician- or other user-programmed change to the operating mode or operating parameters of individual nodes or implementation of a next generation operating system or software updates applied to the existing nodes. Automatic reconfiguration occurs by returning to learning process block 210 wherein the current routing scheme 220, node roles 225 and channel plan 230, variable rules included in the network rule set 200, and in some cases constant rules included in the network rule set 200, are adjusted "on-the-fly" to meet current power source capacities, communication priorities, therapy readiness needs, sensing demand, and data throughput requirements. Although learning process block 210 and normal operations block 235 are illustrated as two distinct blocks in FIG. 4, the learning process/reconfiguration operations of the network are operating in a continuous dynamic manner in response to changes in the network operating conditions or environment.

A change in the status of individual nodes (block 240) can cause dynamic adjustment of the behavior of each node. Individual node status considers both power status and operational workload for any primary functions related to sensing and/or therapy delivery. A change in power status or device workload can result in adjustments to node roles and assignments as well as altering network communication behavior. A node can rescind a specialist role as a function of its power status or an increase in its sensing or therapy workload. Network communication behavior of a node may be altered in response to a change in node status by reducing communication frequency and/or reducing message length and content. A node entering a low-power status or reaching end-of-life may generate messages in a "last gasp" format. Abbreviated messages and message formatting allows power status and impending node death to be communicated through the network. Predictive and preemptive reconfigurations of node assignments, channel plan, and routing scheme for the surviving network membership may be made in response to such messages.

During normal operation 235, nodes will each maintain routing quality information summarizing communications success metrics. This routing quality information will be distributed throughout the network or with specialist nodes on a periodic basis such that a network reconfiguration may occur if routing quality diminishes. Dynamic optimization and adaptation algorithms will drive network changes to optimize operational efficiency and reliability of both local and global mesh network performance.

An external change to the network rule set (block 245) will trigger a reconfiguration process such that the node roles 225, routing scheme 220, and channel plan 230 can be redefined in accordance with the new rules.

The network membership (block 250) may change as new devices are introduced or removed. New devices may be implanted or positioned externally to the patient within communication proximity (which may be on a "coming and going" basis as the patient moves about). Existing devices may be removed from the network due to power loss, deactivation, or physical removal. An existing network may come into contact with a second mesh network, for example networked external monitoring devices in a hospital setting, and the networks may merge. As such, a membership change triggers a reconfiguration process in which the node roles 225, routing scheme 220 and channel plan 230 are adjusted. In some cases, communication with an adjacent network may cause self-isolation of the mesh network for patient safety and security using, for example, frequency or time multiplexing or a logical group identification code.

The network may also respond to a change in patient status (block 255). Communication priorities, power allocations, and device operating status may all change in response to a change in patient status, which may be an adverse physiological event or a worsening, improving or changing physiological condition.

Changes in node status, rule set, network membership, and patient status may occur in unpredictable and frequent manner. The network responds to these changes by dynamically reconfiguring itself to operate in accordance with the present conditions, even when these conditions may be rapidly changing.

FIG. 4, as well as other diagrams and drawings presented herein are intended to illustrate the functional operation of the mesh network, and should not be construed as reflective of a specific form of software or hardware necessary to practice the invention. It is believed that the particular form of software will be determined primarily by the particular devices employed in the system. Providing software to accomplish the present invention in the context of any modern implantable medical device system, given the disclosure herein, is within the abilities of one of skill in the art.

Figure 5:
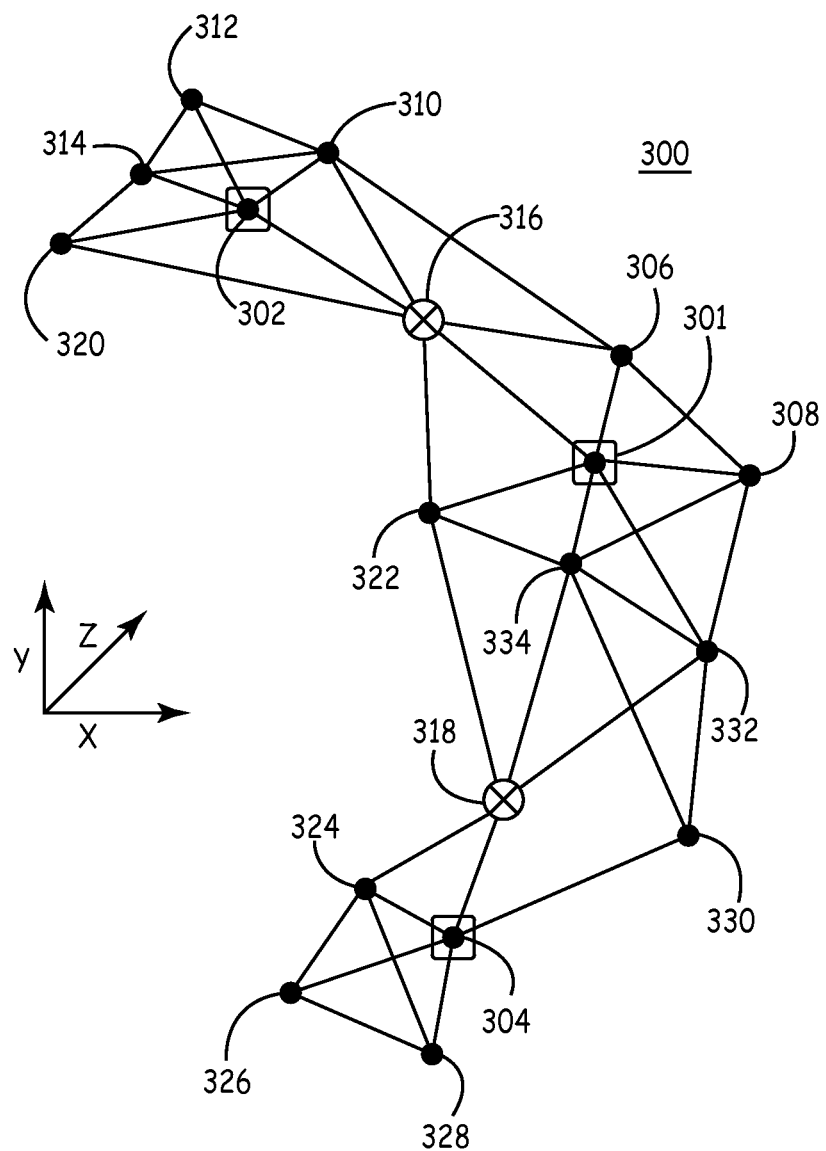
FIG. 5 is a conceptual diagram of a mesh network architecture implemented in an implantable medical device system.

FIG. 5 is a conceptual diagram of a mesh network architecture implemented in an implantable medical device system. The network 300 is an n-dimensional network including nodes 301 through 318 embodied as implantable devices arranged within the three-dimensional space of the patient's body and may include external devices. Fourth and higher order dimensions are represented by specialized dimensional portal nodes 316 and 318 which function as repeater nodes.

Interior nodes can be considered surface nodes because of their proximity to a specialist node (gateway, data processor, data storage, etc.). Specialist nodes 301, 302 and 304 having greater power capacity and processing power can be interspersed through the mesh to provide local "neighborhoods" or clusters of nodes, particularly more remote clusters of nodes, with local data processing or other services. For example, specialist node 302 may provide data processing services for adjacent sensor nodes 310, 312, 314 and 320. Specialist node 302 may transmit processing results back to sensor nodes 310, 312, 314 and 320 as needed thereby providing a short feedback loop. Local specialist nodes can also reduce redundant device functions and potentially reduce parametric data collection for neighboring nodes. Interspersed specialist nodes 301, 302, and 304 may also be assigned the role of "local coordinator" to control communications from remote "neighborhoods" or clusters of nodes to surface or other specialized nodes. Repeater nodes 316 and 318 provide shorter pathways from such remote nodes to interior nodes.

Communication pathways exist between all of nodes 301 through 318 with longer pathways not shown in FIG. 5 for the sake of clarity. Some nodes may be implemented as transmit-only nodes. Transmit-only operation can be supervised by Aloha or other protocols for minimizing collisions of transmitted data packets. Nodes may be enabled to alternate between transmit and transceiver modes of operation dynamically as a function of network operating needs, power status, and patient status.

Node hops or routes used to channel data through the mesh network 300 to a specialist node, e.g., nodes 301, 302 and 304, are dynamically adjusted in response to the mesh depth of a transmitting node, data throughput, and operational overhead. Communication scheduling through long and tortuous routes can be used for low priority communications or infrequent tasks, reserving shorter more efficient routes for higher priority communications. Generally higher priority communications will relate to patient or device-related events or conditions that can impact patient health and safety or otherwise have an adverse affect on disease state or symptoms.

Communication between nodes can be synchronous or asynchronous and security measures such as encryption and data splicing can be used to ensure patient privacy and safety. Nodes can be addressed as an entire group, subset, or individuals. Node groups or individuals can be reconfigured for network functionality or reprogrammed for adjusting primary functionality (reprogramming sensing/therapy delivery operating mode or operating control parameters) from peripheral external nodes by a network administrator. Network configuration and/or programming data are routed through the mesh to the appropriate nodes being addressed. The freshness, redundancy, and frequency of data collection or other data collection and communication operations for network nodes can be altered or adjusted by addressing reconfiguration/programming commands to node groups or individuals. Nodes may be reprogrammed to alter primary sensing/therapy delivery functions in response to changes in patient condition. Nodes may be reconfigured for network operations to reduce power consumption, e.g. while a patient is hospitalized and coupled to external monitoring equipment, to limit mesh depth and force shorter communication pathways or for performing other network optimization operations.

Figure 6:
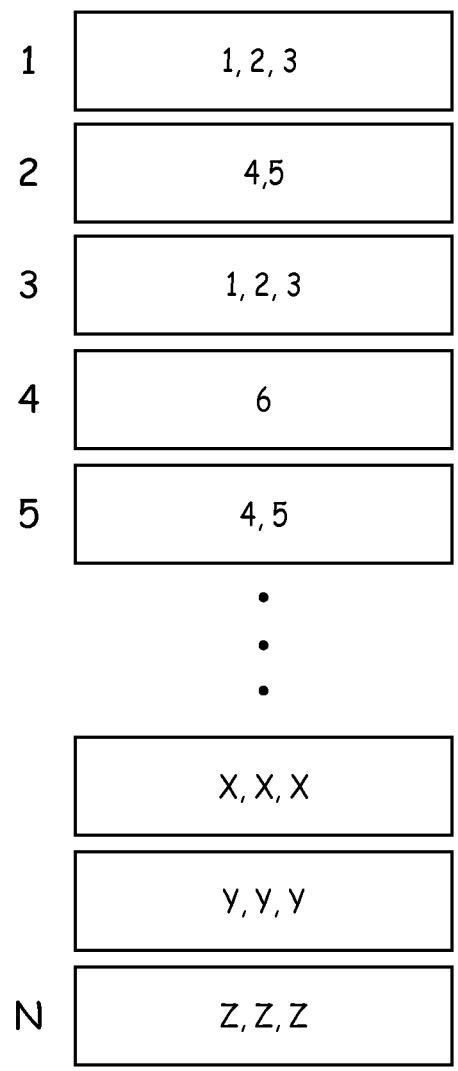
FIG. 6 is a conceptual diagram of a channel plan implemented by the mesh network.

FIG. 6 is a conceptual diagram of a channel plan implemented by the mesh network. The channel plan will include multiple communication channels 1-N which can be divided according to a frequency, time, or code multiplexing. Operating frequency options include MICS, MEDS and ISM bands. Multiple nodes may be assigned to each channel and each node may be assigned to one or more channels. For example, in the fictional example given, nodes 1, 2 and 3 are assigned to channels 1 and 3; nodes 4 and 5 are assigned to channels 2 and 5, and channel 4 is reserved for node 6. Channel assignments will be based on prioritization of communications, frequency and size of communications, and other application specific considerations. Nodes can communicate concurrently on adjacent or distant channels. Access to a channel will be based on message priority and patient condition. A node may alternate between open, restricted, or highly-controlled channels based on message priority and patient status. As described previously, the channel plan can change dynamically based on network membership, individual node power status, patient status, or an external adjustment to the network rule set.

Thus, a mesh network communication system for use with an implantable medical device system has been presented in the foregoing description with reference to specific embodiments. It is appreciated that various modifications to the referenced embodiments may be made without departing from the scope of the invention as set forth in the following claims.

The invention claimed is:

1. An implantable medical device system, comprising:
   multiple implantable medical devices, each of the medical devices having a node status comprising a power status of a power supply of the medical device and an operational workload of the medical device corresponding to a primary function of the medical device;
   means for providing a wireless communication network between the multiple medical devices via multiple communication pathways;
   means for receiving an adjusted network rule set; and
   means for automatically configuring the network wherein the configuring means comprises means for assigning network tasks to the multiple medical devices in response to the node status of each of the medical devices.

2. The system of claim 1 further including an external device in communication with the multiple implanted medical devices via the means for providing wireless communication between the multiple medical devices via multiple communication pathways.

3. The system of claim 1 wherein a communication pathway selected between a first implanted device and a second implanted device of the multiple medical devices comprises at least one of the other of the implanted medical devices.

4. The system of claim 1 wherein at least one of the multiple medical devices is a specialist node assigned to perform a network communication task.

5. The system of claim 4 wherein the specialist node is one of: a gateway node, a data processor node, a data storage node, a police node, a housekeeper node, a algorithm workhorse node, a network administrator node, a scheduler node, a local coordinator node, and a repeater node.

6. The system of claim 1 wherein at least one of the multiple medical devices further comprises a therapy delivery module.

7. The system of claim 1 wherein at least one of the multiple medical devices further comprises a physiological sensor.

8. The system of claim 1 further comprising re-assigning network tasks to the multiple medical devices in response to one of a change in a network rule set, introduction of a new device in the network, removal of an existing device from the network, a change in the primary operating status of a network member, a change in the power status of a network member, and a change in a patient status.

9. The system of claim 1, further comprising means for monitoring a patient condition.

10. The system of claim 1 wherein the adjusted network rule set comprises one or more constant rules and one or more variable rules.

11. The system of claim 1 wherein, in response to the node status of each of the medical devices, the configuring means further comprises one of:
means for defining a channel plan, defining a routing scheme, and configuring the adjusted network rule set.

12. An implantable medical device system, comprising:
a plurality of implantable medical devices, each of the medical devices having a node status derived from a power status of a power supply of the medical device and an operational workload of the medical device associated with a primary function of the medical device;
means for providing a wireless communication network between the multiple medical devices via multiple communication pathways;
means for receiving an adjusted network rule set;
means for evaluating the node status of each of the medical devices to determine one of: a change in a network rule set, introduction of a new device in the network, removal of an existing device from the network, a change in the primary operating status of a network member, a change in the power status of one of the plurality of implantable medical devices, and a change in a patient status; and
means for automatically configuring the network including the plurality of implantable medical devices in response to a result of the evaluation by the means for evaluating the node status, wherein the automatic configuration includes assigning roles to individual ones of the plurality of implantable medical devices for performing network tasks in response to the evaluation of the node status.

13. The implantable medical device system of claim 12 wherein, in response to a result of the evaluation of the node status, the automatic configuration further comprises one of:
defining a channel plan;
defining a network communications routing scheme; and
adjusting a network rule set.

* * * * *